(12) United States Patent
Ryan

(10) Patent No.: US 10,716,472 B2
(45) Date of Patent: *Jul. 21, 2020

(54) DEVICE AND METHOD TO QUANTIFY VITREOUS OPACITY IMPAIRMENT

(71) Applicant: Edwin Ryan, St. Paul, MN (US)

(72) Inventor: Edwin Ryan, St. Paul, MN (US)

(73) Assignee: Edwin Ryan, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/969,459

(22) Filed: May 2, 2018

(65) Prior Publication Data

US 2018/0317767 A1 Nov. 8, 2018

Related U.S. Application Data

(63) Continuation of application No. 15/309,392, filed as application No. PCT/US2015/029506 on May 6, 2015, now Pat. No. 9,974,437.

(60) Provisional application No. 62/062,617, filed on Oct. 10, 2014, provisional application No. 61/989,931, filed on May 7, 2014.

(51) Int. Cl.
*A61B 3/14* (2006.01)
*A61B 3/10* (2006.01)
*A61B 3/15* (2006.01)
*G06T 7/00* (2017.01)
*H04N 5/33* (2006.01)

(52) U.S. Cl.
CPC ............ *A61B 3/145* (2013.01); *A61B 3/1025* (2013.01); *A61B 3/14* (2013.01); *A61B 3/152* (2013.01); *G06T 7/0016* (2013.01); *H04N 5/33* (2013.01); *G06T 2207/10016* (2013.01); *G06T 2207/10048* (2013.01); *G06T 2207/30041* (2013.01)

(58) Field of Classification Search
CPC ........... A61B 3/14; A61B 3/0025; A61B 3/12; A61B 3/102; A61B 3/0058
USPC .................................................. 351/206, 211
See application file for complete search history.

(56) References Cited

U.S. PATENT DOCUMENTS 5,214,455 A * 5/1993 Penney .................... A61B 3/11
351/208
9,974,437 B2 * 5/2018 Ryan ........................ A61B 3/14
(Continued)

FOREIGN PATENT DOCUMENTS

WO WO-2015171793 A1 11/2015

OTHER PUBLICATIONS

"U.S. Appl. No. 15/309,392, Non Final Office Action dated Aug. 29, 2017", 12 pgs.
(Continued)

*Primary Examiner* — Mohammed A Hasan
(74) *Attorney, Agent, or Firm* — Schwegman Lundberg & Woessner, P.A.

(57) ABSTRACT

Examples of devices and method for quantifying opacities in an eye are shown. Examples include analysis of still images or video images. In one example a cross section area of opacities within a visual axis are quantified. Opacities in the vitreous of an eye, such as "floaters" can vary in severity from little or no reduction in vision, to bothersome, to high reduction in visual function. It is desirable to be able to quantify a level of severity of visual obstruction within a patient's eye and proceed with a level of treatment to match the condition.

11 Claims, 5 Drawing Sheets

(56) References Cited

U.S. PATENT DOCUMENTS

| | | | |
|---|---|---|---|
| 2003/0058405 A1* | 3/2003 | Cornsweet | A61B 3/1176 351/212 |
| 2009/0079937 A1* | 3/2009 | Chen | A61B 3/0008 351/210 |
| 2010/0049057 A1 | 2/2010 | Gellerman et al. | |
| 2010/0201944 A1 | 8/2010 | Lewis et al. | |
| 2011/0299034 A1 | 12/2011 | Walsh et al. | |
| 2013/0021575 A1* | 1/2013 | Yoshida | A61B 3/102 351/206 |
| 2013/0215235 A1 | 8/2013 | Russell | |
| 2013/0321775 A1* | 12/2013 | Richter | A61B 3/032 351/221 |
| 2017/0065173 A1 | 3/2017 | Ryan | |

OTHER PUBLICATIONS

"U.S. Appl. No. 15/309,392, Notice of Allowance dated Jan. 19, 2018", 8 pgs.

"U.S. Appl. No. 15/309,392, Response filed Nov. 28, 2017 to Non Final Office Action dated Aug. 29, 2017", 9 pgs.

"International Application Serial No. PCT/US2015/029506, International Search Report dated Aug. 7, 2015", 3 pgs.

"International Application Serial No. PCT/US2015/029506, Written Opinion dated Aug. 7, 2015", 9 pgs.

\* cited by examiner

DEVICE AND METHOD TO QUANTIFY VITREOUS OPACITY IMPAIRMENT

CLAIM OF PRIORITY

This application is a continuation of and claims the benefit of priority under 35 U.S.C. 120 to U.S. patent application Ser. No. 15/309,392, filed on Nov. 7, 2016, which is a U.S. National Stage Filing under 35 U.S.C. 371 from International Application No. PCT/US2015/029506, filed on May 6, 2015, and published as WO2015/171793 A1 on Nov. 12, 2015, which claims the benefit of priority to U.S. Provisional Patent Application Ser. No. 62/062,617, filed on Oct. 10, 2014 and to U.S. Provisional Patent Application Ser. No. 61/989,931, filed on May 7, 2014, each of which is hereby incorporated by reference herein in its entirety.

TECHNICAL FIELD

This invention relates to devices and methods is for ophthalmological procedures.

BACKGROUND

Opacities in the vitreous of an eye, such as "floaters" can vary in severity from little or no reduction in vision, to bothersome, to high reduction in visual function. It is desirable to be able to quantify a level of severity of visual obstruction within a patient's eye and proceed with a level of treatment to match the condition.

DETAILED DESCRIPTION

Figure 1:
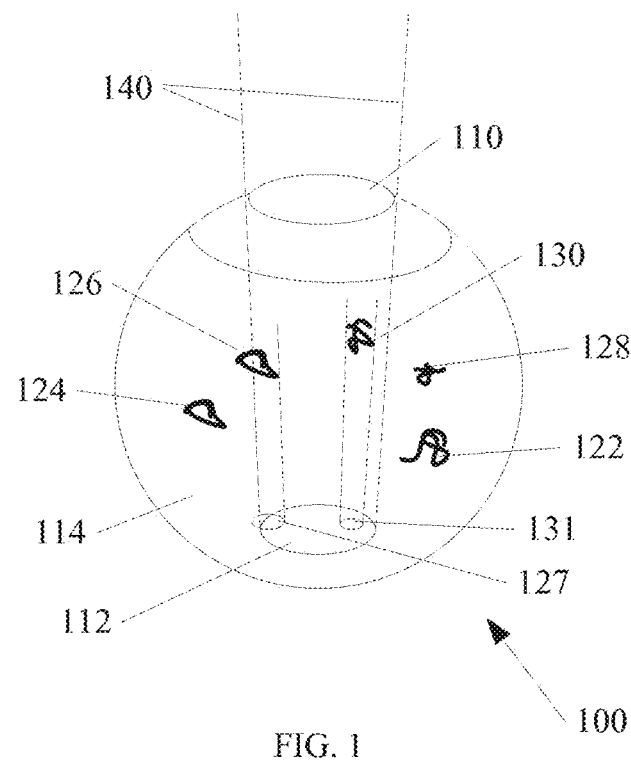
FIG. 1 shows an eye, including a number of opacities according to an embodiment of the invention.

In the following detailed description, reference is made to the accompanying drawings which form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, or logical changes, etc. may be made without departing from the scope of the present invention.

FIG. 1 shows an eye 100 with a cornea 110 at the top, and a central retina area 112 within a bottom portion of the eye 100. A number of opacities 122-130 are shown within a vitreous 114 of the eye. In one example, the number of opacities 122-130 are considered "floaters," however examples of the present invention are equally effective at quantifying other types of opacities, such as blood clots, etc. within the eye 100.

The visual axis 140 is defined by the dashed lines shown. In one example, only select opacities are within the visual axis 140. In the example of FIG. 1, opacity 130 is located entirely within the visual axis 140. The opacity 130 includes a cross section that projects an area 131 onto the central retina area 112. In the example of FIG. 1, the entire area 131 is within the visual axis 140. In addition, opacity 126 is shown with a cross section that projects an area 127. The area 127 is shown with only a portion of the area 127 within the visual axis 140. Other opacities 124, 128 and 122 project a cross section, however in the example of FIG. 1, none of these cross sections is within the visual axis 140.

Figure 2:
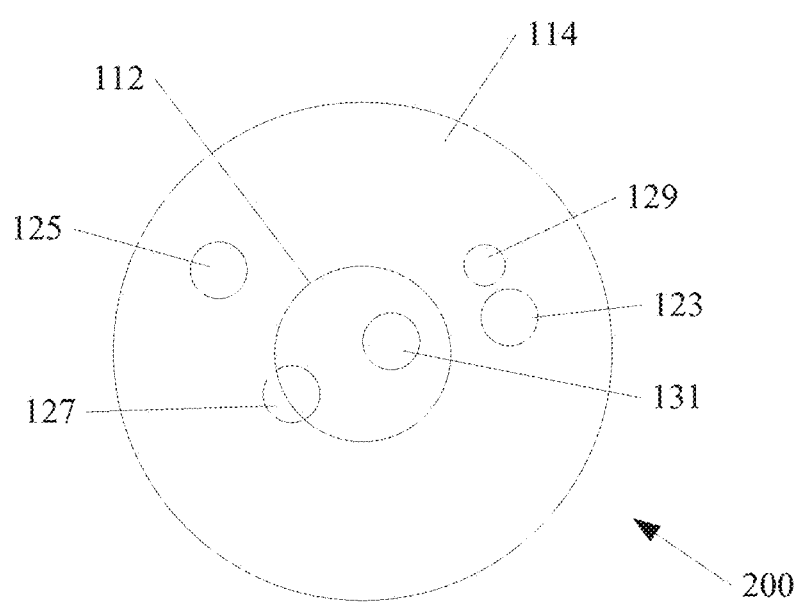
FIG. 2 shows an image of the vitreous of the eye from FIG. 1, according to an embodiment of the invention.

FIG. 2 shows an example image 200 of the vitreous 114 from FIG. 1. The central retina area 112 is shown, and effectively forms the visual axis 140. Any cross section that overlaps the central retina area 112 is within the visual axis 140. As discussed above, area 123 is projected from a cross section of opacity 122, area 125 is projected from a cross section of opacity 124, area 127 is projected from a cross section of opacity 126, area 129 is projected from a cross section of opacity 128, and area 131 is projected from a cross section of opacity 130. As discussed above, area 131 and a portion of area 127 overlap the central retina area 112, and are considered within the visual axis 140.

In one example, an image analysis system is used in conjunction with image 200 to detect the opacities, and their respective area projections. In one example, the image analysis system is used to detect a density of opacities. In one example, the image analysis system is used to determine the blockage of light transmission by individual opacities. For example, software can be used with a digital image to detect darker or lighter regions and/or gradients between regions.

An appropriate algorithm can be used to quantify a cross section area of the opacities within the vitreous. Analysis of the image can also capture an amount of reflectance to calculate a level of opacity (translucence) of individual opacities. In the example of FIG. 2, the cross section area of all opacities would equal an area sum of regions 123, 125, 127, 129 and 131. In one example, the image analysis system further defines the visual axis 140. In one example the retina can be detected from features in the image. In another example, a user can define the visual axis 140 manually using movable boundaries and software.

In one example the image analysis system further quantifies an amount of the cross section area of the opacities that obstruct a retina. In the example of FIG. 2, the cross section area of opacities within the visual axis 140 would include all of region 131, and the portion of region 127 that overlaps the central retina area 112. In another example, any cross section area projected by an opacity that overlaps the central retina area 112 may be counted in its entirety, without accounting for what fraction is within the visual axis 140. While less accurate, this example may be easier to implement with software.

Using devices and methods described above, a cross section area of opacities that impinge on a patient's vision can be quantified and an appropriate treatment or lack of treatment can be chosen. Additionally, using devices and methods described above, a density of opacities that impinge on a patient's vision can be quantified and an appropriate treatment or lack of treatment can be chosen.

In one example output, a color coded image or video can be calculated and displayed. Similar to a cloud cover weather map, very dense opacities may be color coded red to indicate a high level of obstruction, while more translucent opacities may be coded green, with yellow regions indicating an intermediate level of translucence. While these colors are used as an example, clearly other color schemes could be used.

In one example the image 200 is a still image. In other examples, the image 200 includes a video image. Because opacities may only obstruct a patient's vision at one time or another depending on movement of the opacities within the eye and/or movement of the patient's eye itself, it may be useful to quantify an amount of obstruction over time using video analysis when the patient is moving their eye. Similar to the still photo example discussed above regarding FIG. 2, in a video example, each frame, or a sampled number of frames from the video may be analyzed and the sum of each analyzed frame added together to determine a quantified amount of obstruction over time.

Using the video example discussed above, it may be useful to have the patient move their eye in a controlled and repeatable manner in order to more consistently measure an amount of obstruction.

Figure 3:
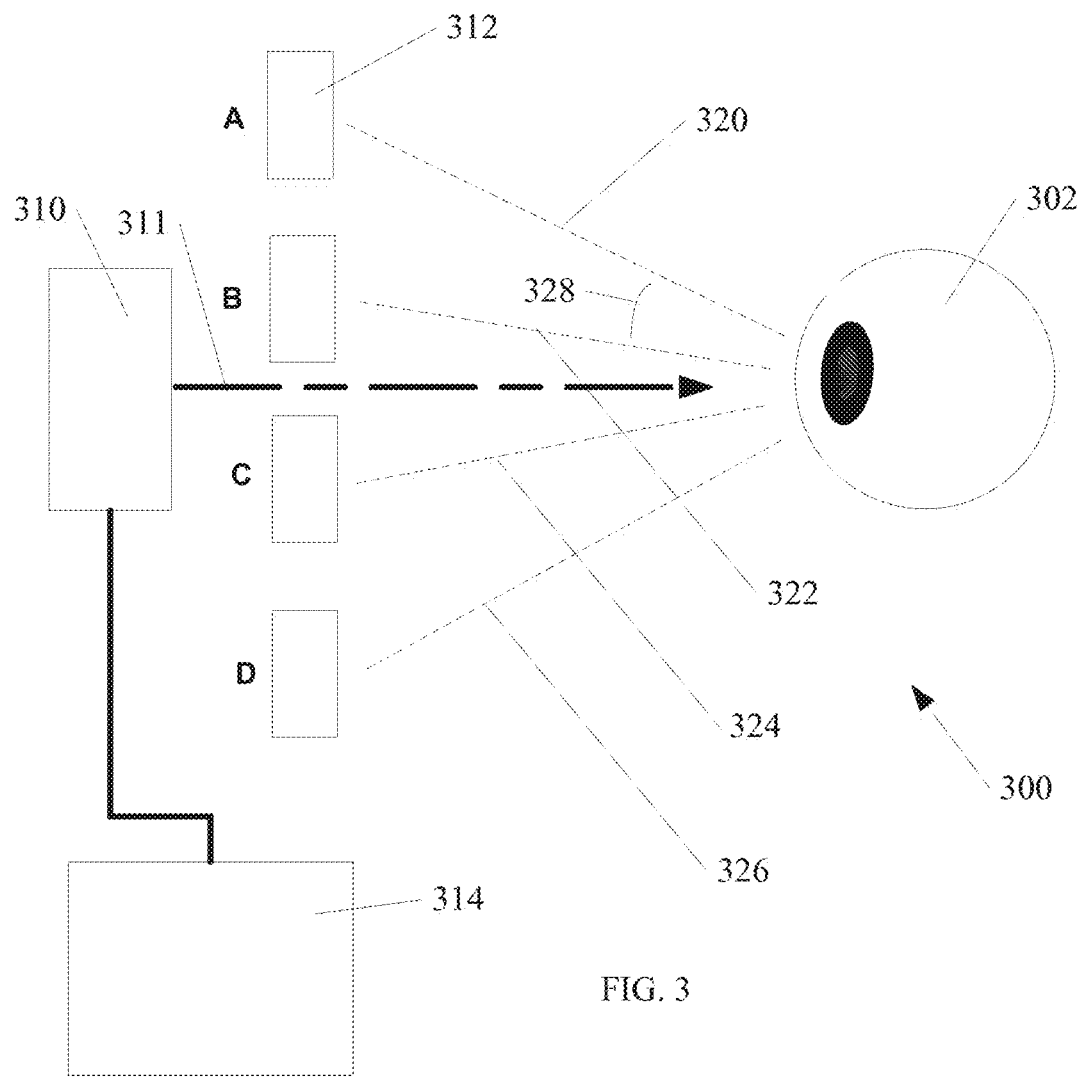
FIG. 3 shows a block diagram of an ophthalmological diagnostic device according to an embodiment of the invention.

FIG. 3 shows an ophthalmological diagnostic device 300 according to an embodiment of the invention. A patient's eye 302 is shown in relation to other block diagram elements of the device 300. One of ordinary skill in the art, having the benefit of the present disclosure will recognize that any number of possible fixtures such as chin guides, forehead pads, etc. may be used to locate the patient's eye 302 within the device 300.

In one example the device 300 further includes an imaging device 310. In one example, the imaging device 310 is an infrared imaging device. Although infrared is used as an example, other wavelengths of light and/or other imaging techniques may be used within the scope of the invention. In one example, the imaging device includes a scanning laser ophthalmoscope (SLO). Although a scanning imager is an example, the invention is not so limited. Non scanning imagers area also within the scope of the invention. The imaging device 310 acquires images of the vitreous within the patient's eye 302 along imaging direction 311.

The device 300 further includes at least one target 312 to align the patient's eye 302 at a desired angular orientation. FIG. 3 shows four possible targets 312 as an example although, as described below, other examples are also within the scope of the invention. The targets 312 align the patient's eye 302 along the illustrated paths 320-326. In one example, one or more mirrors can be used in conjunction with one or more targets to set a target distance, and an individual mirror can be moved to change an orientation of the target with respect to a straight-ahead gaze of the patient.

Multiple selectable target locations A-D are also shown in FIG. 3. In one example a single target 312 is movable between the multiple selectable target locations to align the patient's eye 302 along a selected path 320-326. In another example, multiple targets 312 are located at each target locations A-D, and a selected target 312 is activated, while other targets 312 are deactivated. For example, an LED light may be located at each target location A-D, and only a selected LED light is turned on at a time in order to orient the patient's eye 302 along a selected path 320-326.

Control circuitry 314 is further shown in FIG. 3 to display the target at the multiple target locations A-D. In one example, the control circuitry 314 aligns the patient's eye 302 at a desired target location A-D and also signals the imaging device 310 to image the vitreous at each selected target location A-D.

In one example, images are acquired with the eye stabilized by looking at a fixation target. The eye looks away, then back at the target (for example, a saccade), setting both the clear vitreous and opacities in motion for a few seconds.

Figure 4:
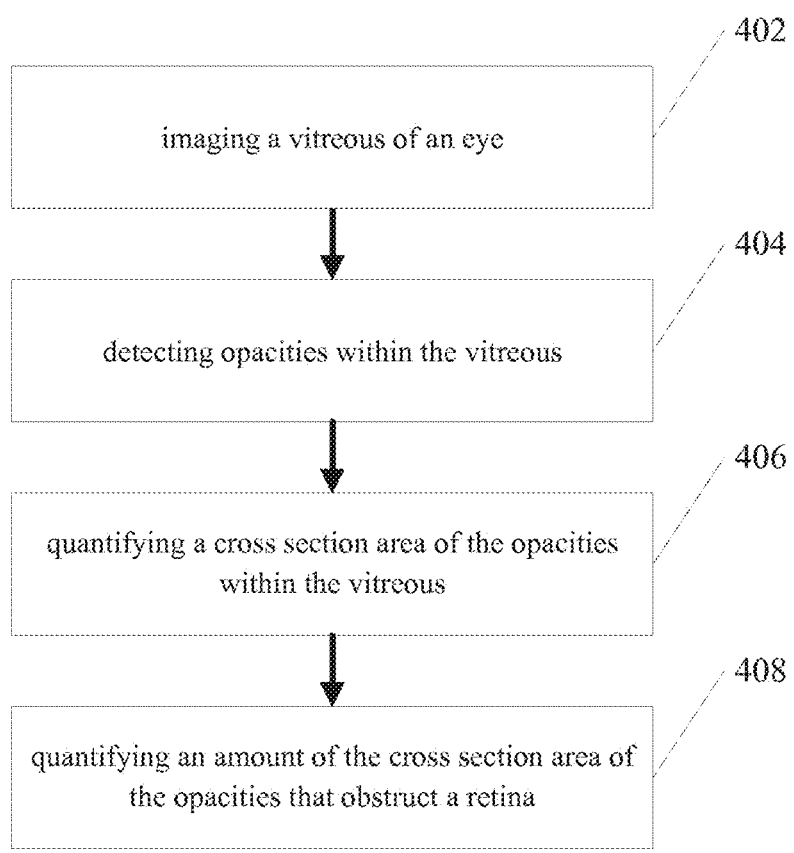
FIG. 4 shows an example method of quantifying opacities according to an embodiment of the invention.

FIG. 4 shows an example method of quantifying opacities in an eye according to an example of the present invention. In operation 402 the vitreous cavity of an eye is imaged. In operation 404, opacities are detected within the vitreous. In operation 406, a cross section area of the opacities is quantified within the vitreous, and in operation 408, an amount of the cross section area of the opacities that obstruct the central retina is quantified.

Figure 5A:
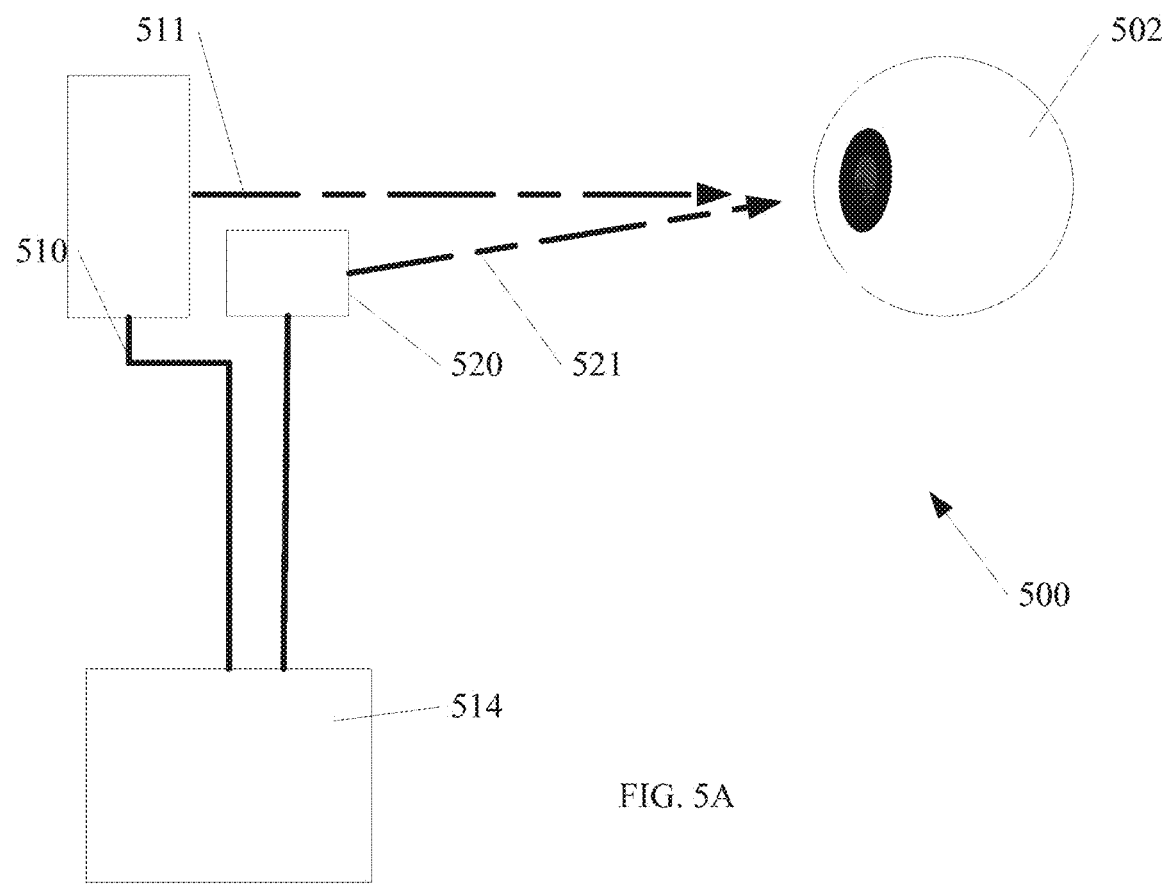
FIG. 5A shows a block diagram of another ophthalmological diagnostic device according to an embodiment of the invention.

FIG. 5A shows an ophthalmological diagnostic device 500 according to an embodiment of the invention. A patient's eye 502 is shown in relation to other block diagram elements of the device 500. One of ordinary skill in the art, having the benefit of the present disclosure will recognize that any number of possible fixtures such as chin guides, forehead pads, etc. may be used to locate the patient's eye 502 in relation to the device 500.

In one example the device 500 further includes an imaging device 510. In one example, the imaging device 510 is an infrared imaging device. Although infrared is used as an example, other wavelengths of light and/or other imaging techniques may be used within the scope of the invention. In one example, the imaging device includes a scanning laser ophthalmoscope (SLO). Although a scanning imager is an example, the invention is not so limited. Non scanning imagers area also within the scope of the invention. The imaging device 510 acquires images of the vitreous within the patient's eye 502 along imaging direction 511.

A projector 520 is further shown in the device 500 of FIG. 5A. In one example, the projector is configured to project text onto at least a portion of the retina. In one example, the projector includes a scanning laser projector. In the example shown in FIG. 5, the projector 520 is a separate component of the device 500, although the invention is not so limited. In one example, the projector 520 is integrated with the imaging device 510. In one example, a scanning laser ophthalmoscope (SLO) is adapted to both project text onto at least a portion of the retina, and provide an imaging function sufficient to quantify obstructions in a patient's vitreous, such as floaters discussed in examples above.

Figure 5B:
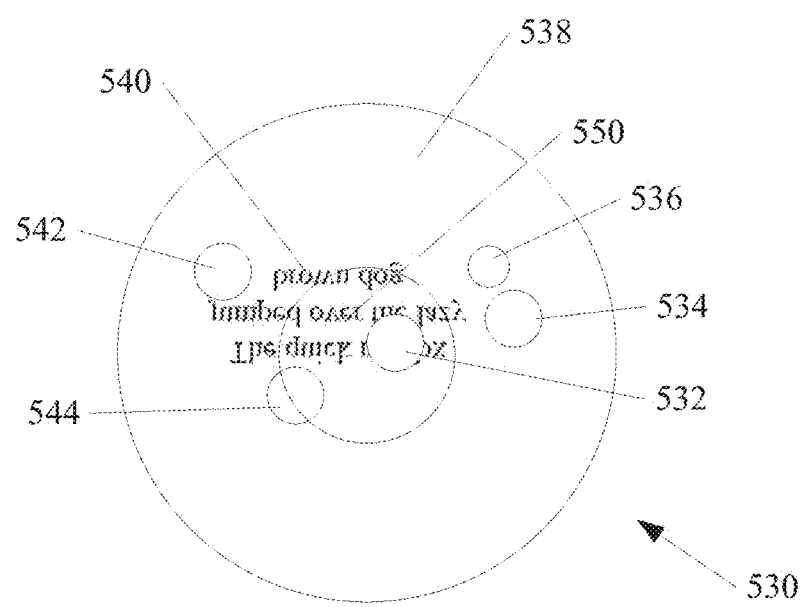
FIG. 5B shows an example image according to an embodiment of the invention.

FIG. 5B shows an example image 530 of the vitreous 538 using the device 500 of FIG. 5. The central retina area 540 is shown, and effectively forms the visual axis, similar to the visual axis 140 from FIG. 1. Any cross section that overlaps the central retina area 540 is within the visual axis. Projected areas 532, 534, 536, 542, and 544 are caused by opacities within the vitreous. One technical challenge with evaluation of a patient with opacities is that some opacity locations within a vitreous do not significantly affect a patient's quality of vision, while other opacity locations may significantly impair quality of vision. However, quantifying an effect of opacities can be difficult because the opacities may move within the vitreous over time, and results of a test to quantify a quality of vision may change over time, and with motion of the eye and/or vitreous. It is desirable to quantify a quality of vision using a practical and repeatable test.

FIG. 5B illustrates an amount of text 550 that is projected within a patient's eye, onto at least a portion of the retina area 540. In the example shown, the text is projected upside down to correspond to the way text would be imaged naturally when focused on the retina area 540. Although text is used as an example, any collection of symbols that can be read or otherwise deciphered in order may be used. As illustrated in FIG. 5B, a portion of the text 550 is obscured by projected area 532 from an opacity within the vitreous 538.

In one method of quantification of quality of vision, a patient reads the text 550 during evaluation over a period of time. Due to the size and location of the text 550, in one example the patient must move their eye over time in order to read the text, or otherwise decipher symbols. The eye motion will cause the vitreous to move, and will cause the projected areas of any opacities to cause different obstructions of the text 550 over time.

Figure 6:
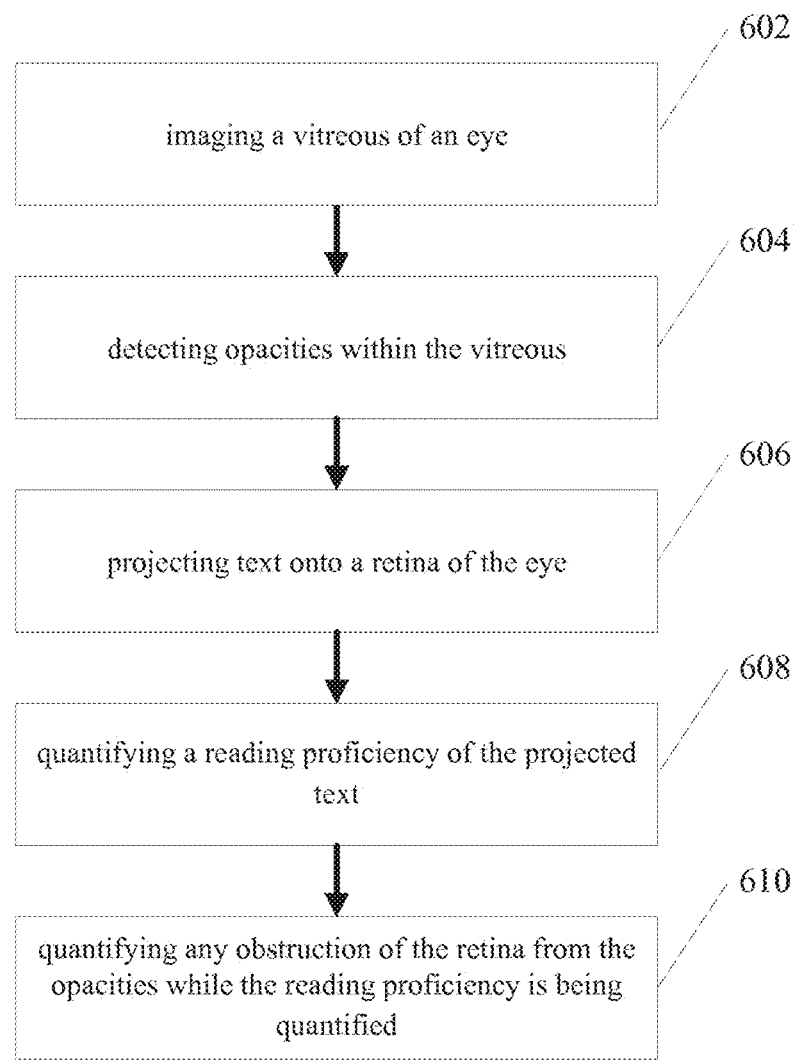
FIG. 6 shows another example of quantifying opacities according to an embodiment of the invention.

FIG. 6 shows a flow diagram of one example method of evaluation of quality of vision that provides a quantifiable result. In operation 602, an imaging device is used to image a vitreous of an eye that includes some amount of opacities within the vitreous. In operation 604, opacities are detected. In the examples discussed above, the detection is based on an amount of obstruction within a visual axis. In one example, the amount of obstruction is quantified based on area measurements of projected areas from opacities compared with a total retina area 540, or other suitable repeatable area.

In operation 606, text is projected onto at least a portion of the retina, as described above in relation to FIGS. 5A and 5B. In operation 608, a reading proficiency of the projected text is quantified. In one example, reading proficiency is quantified as reading speed. Other possible factors for quantification may include, but are not limited to reading accuracy, symbol identification, etc. Combinations of speed and accuracy are also possible. In operation 610, the amount of obstruction over time while reading the text is quantified based on area measurements of projected areas from opacities compared with a total retina area 540, or other suitable repeatable area.

By combining both a reading test and quantification of an amount of obstruction over time, a very accurate and repeatable test is provided to evaluate a quality of vision in a patient with opacities in their vitreous. The reading test is a very practical test of what a patient will experience in daily activity. The motion of the vitreous and any opacities caused by reading will provide quantifiable data for opacities that may not have factored in to a static test because at any single given time, selected opacities may be in a periphery of the vitreous. However, when evaluated over time, due to eye motion reading text, these opacities that would hove been missed, are included in the overall evaluation of the patient.

In one example to encourage controlled eye movement, the text 550 is projected in an area larger than the retina area 540, as shown in FIG. 5B. An area of the text can be chosen in a repeatable size to control an amount of eye movement to provide a repeatable test. In one example, the text 550 is moved over time to different locations over the retina area 540 to encourage controlled eye movement. By controlling the locations of the text 550, the eye motion is controllable to provide a repeatable test.

To better illustrate the method and device disclosed herein, a non-limiting list of embodiments is provided here:

Example 1 includes an ophthalmological diagnostic device. The device includes a vitreous imager, an image analysis system configured to detect opacities within a vitreous, and a retina analysis system configured to quantify an amount of obstruction of the retina from the opacities.

Example 2 includes the ophthalmological diagnostic device of example 1, wherein the vitreous imager is configured to capture still photo images.

Example 3 includes the ophthalmological diagnostic device of any one of examples 1-2, wherein the vitreous imager is configured to capture and record video images.

Example 4 includes the ophthalmological diagnostic device of any one of examples 1-3, wherein the retina analysis system is configured to quantify an amount of obstruction of the retina per unit of time over a duration of at least a portion of a video.

Example 5 includes the ophthalmological diagnostic device of any one of examples 1-4, further including a number of controlled targets to direct a patient's eye in a controlled way during a video image capture.

Example 6 includes the ophthalmological diagnostic device of any one of examples 1-5, wherein the vitreous imager includes an infrared spectrum imager.

Example 7 includes a method including imaging a vitreous of an eye, detecting opacities within the vitreous, quantifying a cross section area of the opacities within the vitreous, and quantifying an amount of the cross section area of the opacities that obstruct a retina.

Example 8 includes the method of example 7, wherein imaging the vitreous of the eye includes infrared imaging.

Example 9 includes the method of any one of examples 7-8, wherein imaging the vitreous of the eye includes still photographic imaging.

Example 10 includes the method of any one of examples 7-9, wherein imaging the vitreous of the eye includes video imaging.

Example 11 includes the method of any one of examples 7-10, wherein quantifying the amount of the cross section area of the opacities that obstruct the retina includes quantifying an amount of obstruction over time in a video.

Example 12 includes the method of any one of examples 7-11, further including directing a patient to look from one direction to another in a controlled manner during video imaging.

Example 13 includes an ophthalmological diagnostic device, comprising a vitreous imager, an image analysis system configured to detect opacities within a vitreous, a projector to project text onto a retina, and a retina analysis system configured to quantify an amount of obstruction of the retina from the opacities.

Example 14 includes the device of example 13, wherein the projector includes a scanning laser projector.

Example 15 includes the device of examples 13-14, wherein the projector is integrated with the vitreous imager.

Example 16 includes the device of any one of examples 13-15, wherein the projector is configured to move a projection location to different portions of the retina.

Example 17 includes the device of any one of examples 13-16, further including a testing system to quantify a patient's reading proficiency of the projected text.

Example 18 includes the device of any one of examples 13-17, wherein the testing system uses a number of factors to quantify a patient, the factors chosen from a group consisting of; an amount of obstruction of the retina from the opacities over time; a reading speed of the projected text; an amount of movement of the projected text; and an amount of movement of the vitreous.

Example 19 includes an evaluation method, comprising imaging a vitreous of an eye, detecting opacities within the vitreous, projecting text onto a retina of the eye, quantifying a reading proficiency of the projected text, and quantifying any obstruction of the retina front the opacities while the reading proficiency is being quantified.

Example 20 includes the method of claim 19, wherein projecting text onto a retina of the eye includes moving text to different locations over the retina during the evaluation method.

Example 21 includes the method of any one of examples 19-20, wherein quantifying a reading proficiency includes quantifying a reading speed.

Example 22 includes the method of any one of examples 19-21, wherein a quantified evaluation score includes a factor of amount of obstruction over time.

Example 23 includes the method of any one of examples 19-22, wherein a quantified evaluation score includes a factor of an amount of vitreous movement.

Example 24 includes the method of any one of examples 19-23, wherein a quantified evaluation score includes a factor of an amount of projected text movement.

Example 25 includes the method of any one of examples 19-24, wherein projecting text onto the retina of the eye include scanning text onto a retina of the eye using a laser.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An ophthalmological diagnostic device, comprising:
a vitreous imager;
an image analysis system configured to detect opacities within a vitreous;
an eye motion guide system configured to controllably and repeatably move a patients eye during imaging; and
a retina analysis system configured to quantify an amount of obstruction of the retina from the opacities over multiple orientations resulting from the eye motion guide system.

2. The ophthalmological diagnostic device of claim 1, wherein the vitreous imager is configured to capture still photo images.

3. The ophthalmological diagnostic device of claim 1, wherein the vitreous imager is configured to capture video.

4. The ophthalmological diagnostic device of claim 1, wherein the eye motion guide system includes a number of controlled targets to direct a patient's eye in a controlled way.

5. The ophthalmological diagnostic device of claim 1, wherein the vitreous imager includes an infrared spectrum imager.

6. An ophthalmological diagnostic device, comprising:
a vitreous imager;
an image analysis system configured to detect opacities within a vitreous;
a projector to project text onto a retina, wherein reading the text is configured to produce controlled eye movement; and
a retina analysis system configured to quantify an amount of obstruction of the retina from the opacities over multiple orientations resulting from the controlled eye movement.

7. The ophthalmological diagnostic device of claim 6, wherein the projector includes a scanning laser projector.

8. The ophthalmological diagnostic device of claim 6, further including a testing system to quantify a patient's reading proficiency of the projected text.

9. An evaluation method, comprising:
imaging a vitreous of an eye;
detecting opacities within the vitreous;
projecting text onto a retina of the eye;
quantifying a reading proficiency of the projected text; and
quantifying any obstruction of the retina from the opacities while the reading proficiency is being quantified; wherein a quantified evaluation score includes a factor of amount of obstruction over multiple orientations of the eye.

10. The evaluation method of claim 9, wherein a quantified evaluation score includes a factor of an amount of projected text movement.

11. The evaluation method of claim 9, wherein projecting text onto the retina of the eye include scanning text onto a retina of the eye using a laser.

* * * * *